(12) United States Patent
Sugo et al.

(10) Patent No.: US 8,048,978 B2
(45) Date of Patent: Nov. 1, 2011

(54) SILPHENYLENE COMPOUND AND PROCESS FOR PRODUCING THE SAME

(75) Inventors: Michihiro Sugo, Annaka (JP); Takahiro Goi, Annaka (JP); Tomoyuki Goto, Annaka (JP); Shohei Tagami, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 372 days.

(21) Appl. No.: 12/332,924

(22) Filed: Dec. 11, 2008

(65) Prior Publication Data

US 2009/0156753 A1    Jun. 18, 2009

(30) Foreign Application Priority Data

Dec. 14, 2007   (JP) .............................. P. 2007-323032

(51) Int. Cl.
*C08G 77/12* (2006.01)

(52) U.S. Cl. .......................................... 528/31; 528/26

(58) Field of Classification Search ............ 528/31, 528/26
See application file for complete search history.

(56) References Cited

U.S. PATENT DOCUMENTS 4,605,567 A    8/1986  Müller et al.
5,461,088 A  * 10/1995  Wolf et al. .................... 522/103

FOREIGN PATENT DOCUMENTS

JP         61-157531 A    7/1986
JP         5-331291 A    12/1993

* cited by examiner

*Primary Examiner* — Kuo-Liang Peng
(74) *Attorney, Agent, or Firm* — Birch, Stewart, Kolasch & Birch, LLP

(57) ABSTRACT

The present invention relates to a silphenylene compound represented by the following formula (1):

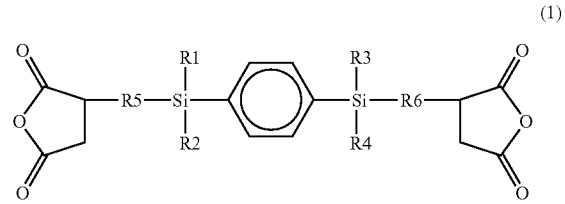

(1)

in which R1 to R4 each independently represents a hydrogen atom or a monovalent hydrocarbon group having 1 to 6 carbon atoms, and R5 and R6 each independently represents a divalent hydrocarbon group having 2 to 8 carbon atoms. The silphenylene compound of the present invention is useful as a flexible printed wiring board material, a passivation film for IC chips, and a panel material for liquid crystals.

4 Claims, 1 Drawing Sheet

SILPHENYLENE COMPOUND AND PROCESS FOR PRODUCING THE SAME

CROSS-REFERENCE TO RELATED APPLICATION

This application is based on Japanese patent application No. 2007-323032 filed on Dec. 14, 2007, the entire contents thereof being hereby incorporated by reference.

FIELD OF THE INVENTION

The present invention relates to a novel silphenylene compound. More specifically, it relates to a novel silphenylene compound useful as a modifier for polyimide resins, polyamide resins, epoxy resins, and the like and to a process for producing the compound.

BACKGROUND OF THE INVENTION

Polyimide resins and the like are known as resins having heat resistance, burning resistance, electrical and mechanical properties, and the like and have been widely used as composite materials for copper-plate laminate sheets and multilayer printed wiring board materials. Polyimide resins have also been utilized as passivation films for multilayer wiring of LSI, α-ray shielding films for memory elements, multilayer wiring insulating films such as magnetic heads, and varnishes for liquid crystal orientation films and the like and also as films for flexible printed wiring boards and the like.

However, the polyimide resins lack self-adhesiveness to metals such as silicon and copper and inorganic materials such as glass and solubility thereof is limited only to high boiling polar solvents as well as viscosity as varnish is high and cured products thereof show high melting points, so that the resins have such disadvantages that they lack moldability and processability. Therefore, it is desired to modify them so as to be applicable to more diversified uses.

Conventionally, as silicon-based compounds having a succinic anhydride moiety, there are known succinic anhydride-modified silicones obtained by subjecting an organohydrogenpolysiloxane and a succinic anhydride having an unsaturated group to an addition reaction through hydrosilylation (Patent Documents 1 and 2).

Patent Document 1: JP-A-61-157531
Patent Document 2: JP-A-5-331291

SUMMARY OF THE INVENTION

An object of the invention is to provide a novel silphenylene compound in which a succinic anhydride derivative is added to a silane compound and a process for producing the same.

As a result of extensive studies for achieving the above object, the present inventors have found a silphenylene compound represented by the following formula (1) and a process for producing the same.

Namely, the present invention provides the following items 1 to 6.

1. A silphenylene compound represented by the following formula (1):

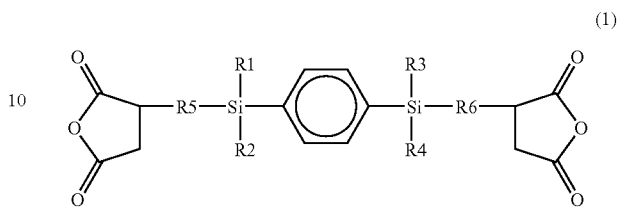

wherein R1 to R4 each independently represents a hydrogen atom or a monovalent hydrocarbon group having 1 to 6 carbon atoms, and R5 and R6 each independently represents a divalent hydrocarbon group having 2 to 8 carbon atoms.

2. The silphenylene compound according to item 1 above, wherein R1 to R4 each represents a methyl group.

3. The silphenylene compound according to item 1 above, wherein R5 and R6 each independently represents an ethylene group or an n-propylene group.

4. A process for producing the silphenylene compound according to item 1 above, which comprises subjecting to an addition reaction a silane compound represented by the following formula (2):

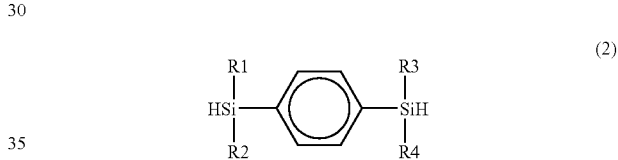

wherein R1 to R4 each independently represents a hydrogen atom or a monovalent hydrocarbon group having 1 to 6 carbon atoms, and a succinic anhydride represented by the following formula (3):

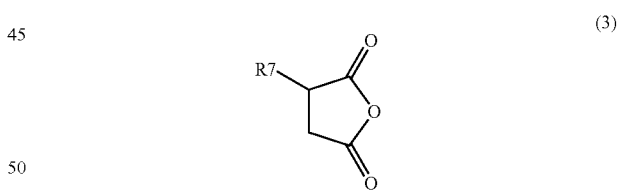

wherein R7 represents a monovalent hydrocarbon group having 2 to 8 carbon atoms and containing an unsaturated group.

5. A polyimide resin produced by using the silphenylene compound according to item 1 above as a monomer.

6. The polyimide resin according to item 5 above, which is produced through a process using an addition reaction or a polycondensation reaction.

When the novel silphenylene compound of the invention is used in polyimides, polyamides, epoxy resins, or the like, it contributes to an improvement in adhesiveness to substrates, heat resistance, and mechanical strength. Therefore, it is useful as a flexible printed wiring board material, a passivation film for IC chips, and a panel material for liquid crystals. Since the novel silphenylene compound of the invention has structurally a silphenylene skeleton, it is considered to be excellent in terms of heat resistance.

DETAILED DESCRIPTION OF THE INVENTION

Figure 1:
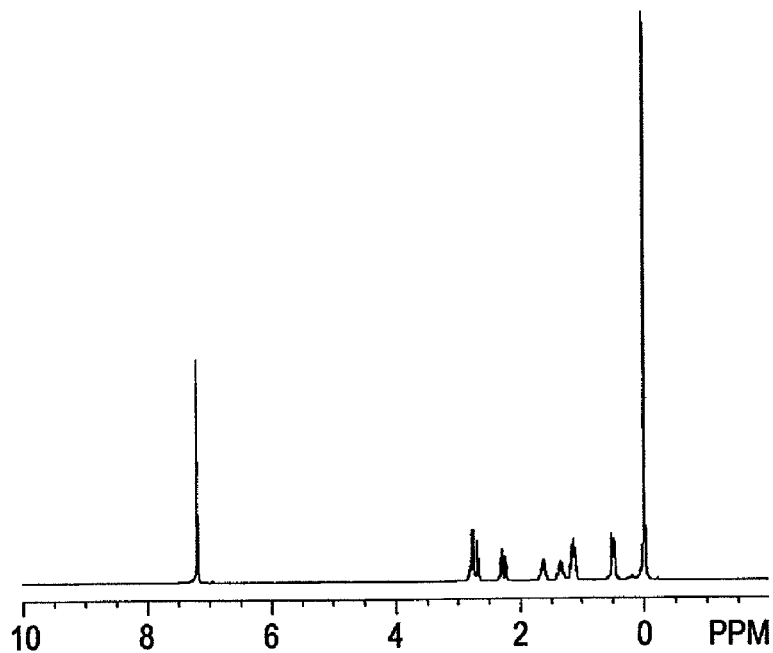
FIG. 1 is a ¹H-NMR chart of the silphenylene compound of Example 1.

The novel silphenylene compound of the invention is represented by the following formula (1):

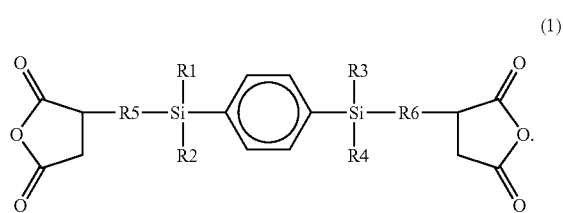

In the formula (1), R1 to R4 each independently represents a hydrogen atom or a monovalent hydrocarbon group having 1 to 6 carbon atoms. As such a monovalent hydrocarbon group, there may be mentioned alkyl groups such as a methyl group, an ethyl group, a propyl group, an isopropyl group, a butyl group, an isobutyl group, an octyl group, and a cyclohexyl group; and aryl groups such as a phenyl group, a tolyl group, and a naphthyl group. Of these, a methyl group is preferred in view of availability of raw materials.

In the formula (1), R5 and R6 each independently represents a divalent hydrocarbon group having 2 to 8 carbon atoms. As such a divalent hydrocarbon group, there may be mentioned an ethylene group, an n-propylene group, an isopropylene group, an n-butylene group, an n-octylene group, a pentylene group, a hexylene group, and the like. Of these, an ethylene group or an n-propylene group is preferred in view of economical efficiency.

The production process of the invention is a process for obtaining the above silphenylene compound by subjecting a silane compound represented by the following formula (2) and a succinic anhydride derivative represented by the following formula (3) to an addition reaction through hydrosilylation:

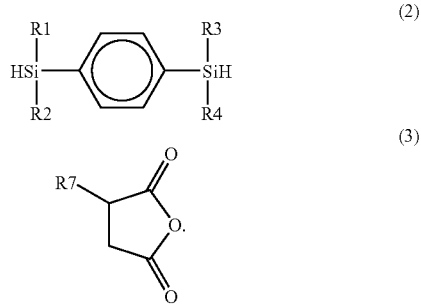

In the formula (2), R1 to R4 are the same as defined in the formula (1) and each independently represents a hydrogen atom or a monovalent hydrocarbon group having 1 to 6 carbon atoms. As specific examples of the silane compound (2), there may be mentioned 1,4-bis(dimethylsilyl)benzene, 1,4-bis(diethylsilyl)benzene, 1,4-bis(diphenylsilyl)benzene, 1,4-bis(methylphenylsilyl)benzene, and the like.

In the formula (3), R7 represents a monovalent hydrocarbon group having 2 to 8 carbon atoms and containing an unsaturated group. As such a hydrocarbon group, there may be mentioned a vinyl group, an allyl group, a hexenyl group, an octenyl group, an acryloylpropyl group, an acryloylmethyl group, a methacryloylpropyl group, a cyclohexenylethyl group, and the like. Of these, a vinyl group or an allyl group is preferred in view of economical efficiency. In this connection, R7 corresponds each of R5 and R6 in the formula (1). As specific examples of the compound represented by the formula (3), there may be mentioned allylsuccinic anhydride, vinylsuccinic anhydride, and the like.

The catalyst to be used in the hydrosilylation reaction may be a catalyst hitherto known and, for example, a platinum-based catalyst such as platinum carbon, chloroplatinic acid, an alcohol solution of chloroplatinum acid, an olefin complex of platinum, an alkenylsiloxane complex of platinum, a carbonyl complex of platinum; a rhodium-based catalyst such as tris(triphenylphosphine)rhodium; an iridium-based catalyst such as bis(cyclooctadienyl)dichloroiridium is suitably used. The amount of the above-mentioned catalyst for the addition reaction to be used may be an effective amount as a catalyst and is not particularly limited but is usually about 0.0001 to 20 parts by weight, preferably about 0.001 to 5 parts by weight based on 100 parts by weight of the total amount of the above-mentioned silane compound and succinic anhydride derivative.

The above-mentioned addition reaction proceeds without using any solvent but the reaction can be carried out under milder conditions with using a solvent. As the solvent, there may be mentioned aromatic hydrocarbon solvents such as toluene and xylene, aliphatic hydrocarbon solvents such as hexane and octane, ethereal solvents such as tetrahydrofuran and dioxane, and the like. They may be used singly or as a combination of two or more thereof. The reaction temperature is 20° C. to 150° C., preferably 50° C. to 120° C. and the reaction time may be about 1 hour to 24 hours. The amount of the succinic anhydride derivative to be used may be 1.0 to 1.2 mol with respect to 1 mol of the Si—H group in the silane compound.

The thus-obtained silphenylene compound of the invention is useful as a modifier for resins such as polyimide resins, polyamide resins, and epoxy resins. When these resins are produced by using the silphenylene compound of the invention as a monomer, heat resistance is particularly improved. In this connection, the content of the silphenylene compound of the invention in the above resin is preferably 5 to 80% by weight.

As the process for producing various resins using the silphenylene compound of the invention as a monomer, a variety of processes may be mentioned and, for example, processes using an addition reaction, a polycondensation reaction, and the like may be mentioned.

EXAMPLES

Example 1

Synthesis of Silphenylene Compound

Into a 500 ml flask fitted with a stirrer, a thermometer, and a condenser were charged 101.6 g (0.726 mol) of allylsuccinic anhydride, 1 g of a 2% ethanol solution of chloroplatinic acid, and 150 g of toluene, followed by heating on an oil bath under stirring so that the inner temperature became 70° C. Then, 58.2 g (0.33 mol) of 1,4-bis(dimethylsilyl)benzene was added dropwise over a period of 20 minutes. After the dropwise addition was completed, the whole was stirred at 90° C. for 3 hours. When the resulting reaction product was analyzed by gas chromatography, the peak derived from 1,4-bis(dimethylsilyl)benzene as a starting material had disappeared. The reaction liquid was concentrated under reduced pressure under conditions of 120° C./10 hPa for 5 hours to obtain 143 g (95% yield) of a white solid. As a result of analysis of the white solid by $^1$H-NMR, it was found that the solid was a compound represented by the following structure.

Figure 2:
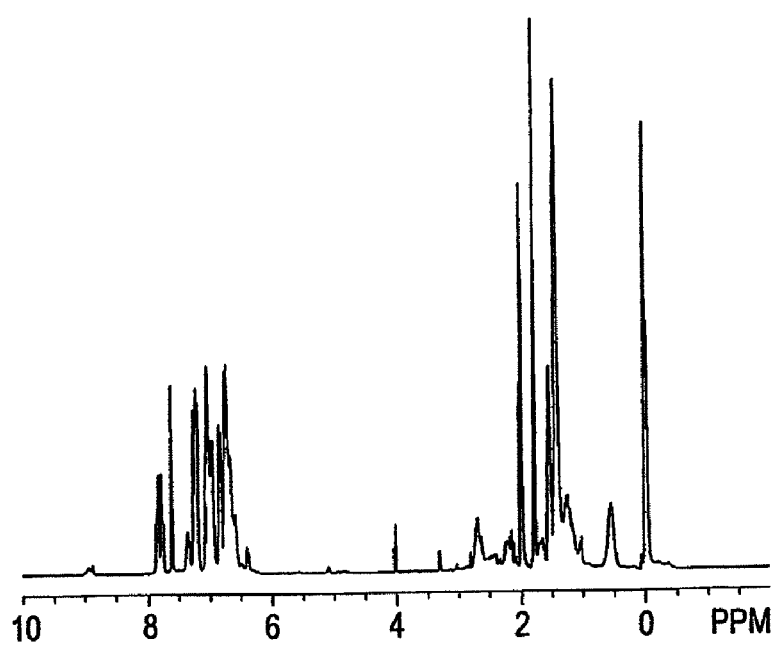
FIG. 2 is a ¹H-NMR chart of the silphenylene-containing polyimide resin of Example 2.

Table 1 and FIG. 1 show $^1$H-NMR chart.

tained for 6 hours, thereby a yellowish brown solution being obtained. After the thus obtained solution was cooled to room temperature (25° C.), it was poured into methanol to effect reprecipitation. When the resulting precipitate was dried and analyzed by NMR, a silphenylene-containing polyimide resin having the following formulae as repeating units was obtained. FIG. 2 shows $^1$H-NMR chart.

When the weight-average molecular weight (in terms of polystyrene) of the resin was measured by gel permeation chromatography (GPC) using N,N-dimethylformamide as a solvent, it was found to be 25000.

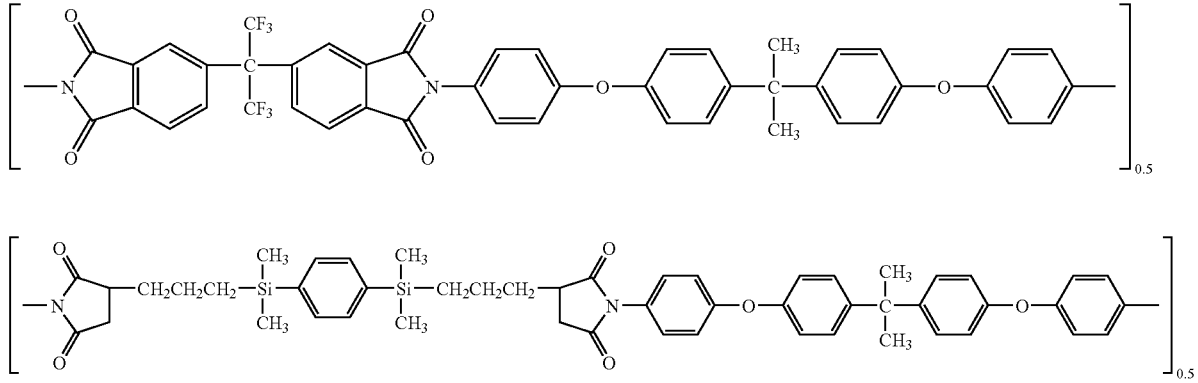

TABLE 1

$^1$H-NMR Measurement

| δ 0.00 ppm | Si—CH$_3$ | 12H |
|---|---|---|
| δ 0.47 to 0.52 ppm | Si—CH$_2$— | 4H |
| δ 1.11 to 1.34 ppm | Si—CH$_2$—CH$_2$— | 4H |
| δ 1.34 to 1.65 ppm | Si—CH$_2$—CH$_2$—CH$_2$ | 4H |
| δ 2.24 to 2.31 ppm | Si—CH$_2$—CH$_2$—CH$_2$—CH | 2H |
| δ 2.68 to 2.82 ppm | Si—CH$_2$—CH$_2$—CH$_2$—CH(C=O)—CH$_2$ | 4H |
| δ 7.20 to 7.21 ppm | Si—Ph | 4H |

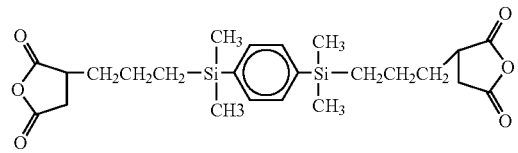

(1-1)

Example 2

Synthesis of Polyimide Resin Containing Silphenylene

Into a flask fitted with a stirrer, a thermometer, and a nitrogen-substituting apparatus were charged 102.5 g (0.25 mol) of 2,2-bis[4-(4-aminophenoxy)phenyl]propane and 500 g of cyclohexanone. Then, 55.5 g (0.125 mol) of 4,4'-hexafluoropropylidenebisphthalic anhydride and 59.3 g (0.125 mol) of the silphenylene compound obtained in Example 1 were added into the above flask while the temperature of the reaction system was regulated so as not to exceed 50° C. The whole was further stirred at room temperature for 8 hours. Then, after a reflux condenser fitted with a water-receiving device was attached thereto, 100 g of xylene was added, the whole was heated to 150° C., and the temperature was maintained for 6 hours, thereby a yellowish brown solution being obtained.

While the present invention has been described in detail and with reference to specific embodiments thereof, it will be apparent to one skilled in the art that various changes and modifications can be made therein without departing from the scope thereof.

What is claimed is:

1. A silphenylene compound represented by the following formula (1):

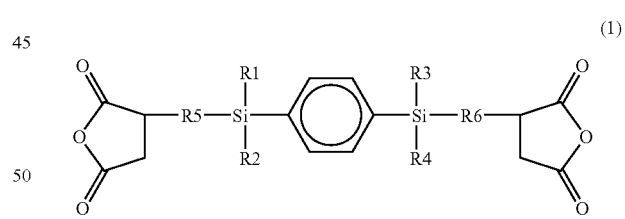

(1)

wherein R1 to R4 each independently represents a hydrogen atom or a monovalent hydrocarbon group having 1 to 6 carbon atoms, and R5 and R6 each independently represents a divalent hydrocarbon group having 2 to 8 carbon atoms.

2. The silphenylene compound according to claim 1, wherein R1 to R4 each represents a methyl group.

3. The silphenylene compound according to claim 1, wherein R5 and R6 each independently represents an ethylene group or an n-propylene group.

4. A process for producing the silphenylene compound according to claim 1, which comprises subjecting to an addition reaction a silane compound represented by the following formula (2):

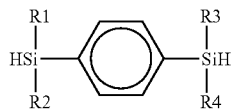

(2)

wherein R1 to R4 each independently represents a hydrogen atom or a monovalent hydrocarbon group having 1 to 6 carbon atoms, and a succinic anhydride represented by the following formula (3):

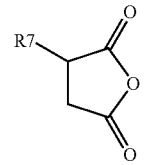

(3)

wherein R7 represents a monovalent hydrocarbon group having 2 to 8 carbon atoms and containing an unsaturated group.

* * * * *